United States Patent
Laursen et al.

[11] Patent Number: 6,138,517
[45] Date of Patent: Oct. 31, 2000

[54] MASS FLOWMETER WITH BIDIRECTIONALLY WOUND OSCILLATION DETECTOR

[75] Inventors: Mogens Bech Laursen, Augustenborg; Henning Max Hansen, Sønderborg; Bertel Birker, Sydals, all of Denmark

[73] Assignee: Danfoss A/S, Nordborg, Denmark

[21] Appl. No.: 09/101,348

[22] PCT Filed: Jan. 17, 1997

[86] PCT No.: PCT/DK97/00023

§ 371 Date: Jul. 6, 1998

§ 102(e) Date: Jul. 6, 1998

[87] PCT Pub. No.: WO97/26508

PCT Pub. Date: Jul. 24, 1997

[30] Foreign Application Priority Data

Jan. 17, 1996 [DE] Germany ........................... 196 01 349
Jun. 11, 1996 [DK] Denmark ............................... 0646/96

[51] Int. Cl.[7] ...................................................... G01F 1/68
[52] U.S. Cl. ................................. 73/861.355; 73/861.356
[58] Field of Search ...................... 73/861.355, 861.356, 73/861.357; 324/207.15, 207.16, 207.17

[56] References Cited

U.S. PATENT DOCUMENTS

| | | | |
|---|---|---|---|
| 4,187,721 | 2/1980 | Smith ................................. | 73/861.356 |
| 4,252,028 | 2/1981 | Smith et al. ........................ | 73/861.355 |
| 4,756,198 | 7/1988 | Levien ................................ | 73/861.355 |
| 4,781,068 | 11/1988 | Pradelli .............................. | 73/861.355 |
| 5,301,557 | 4/1994 | Cage et al. .......................... | 73/861.355 |
| 5,349,872 | 9/1994 | Kalotay et al. ..................... | 73/861.355 |

*Primary Examiner*—Harshad Patel
*Attorney, Agent, or Firm*—Lee, Mann, Smith, McWilliams, Sweeney & Ohlson

[57] ABSTRACT

The invention concerns a mass flowmeter for measurement of the mass and the density of a fluid flowing through a measuring pipe. The mass flowmeter uses the Coriolis principle for establishing mass and density. The mass flowmeter comprises at least one, preferably two, measuring pipes. Each measuring pipe is provided with an oscillation generator and a first oscillation detector and a second oscillation detector. The oscillation generator is meant for making the measuring pipes oscillate, and the oscillation detectors are meant for detecting oscillations in the measuring pipes when fluid flows through the measuring pipes. The oscillation detectors consist of armatures in the form of bar magnets extending into a ring coil. The coil is provided with a first winding and a second winding which are connected in series, and which are arranged at a distance from one another along a longitudinal axis. The first winding is wound in one direction around a longitudinal axis, and the second winding is wound in another, and in relation to the first winding, opposite direction around the longitudinal axis. This means that the measuring accuracy is increased, and at the same time the demand on mounting tolerances is reduced.

11 Claims, 5 Drawing Sheets

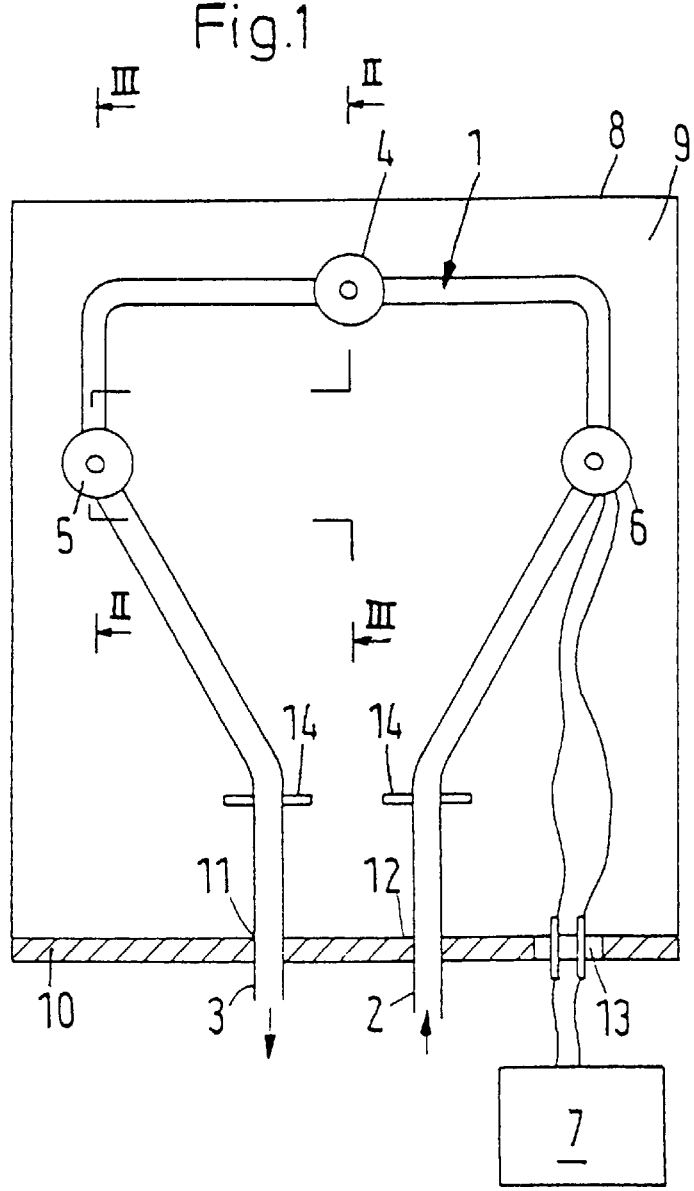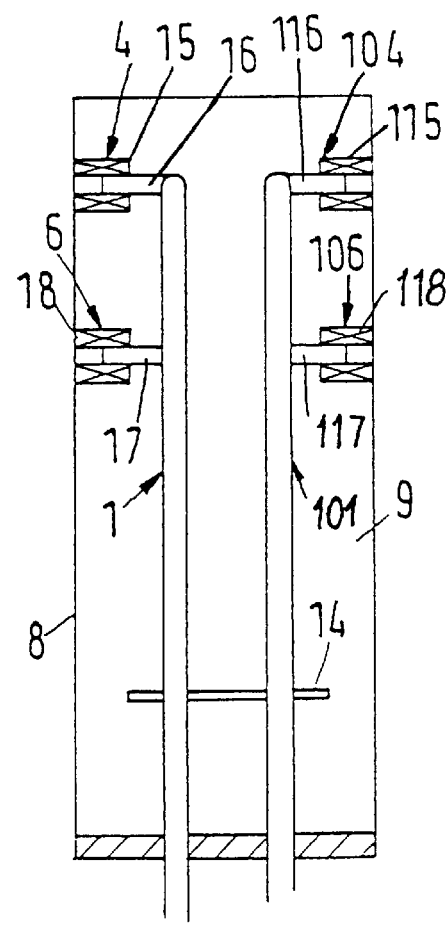

6,138,517

MASS FLOWMETER WITH BIDIRECTIONALLY WOUND OSCILLATION DETECTOR

BACKGROUND OF THE INVENTION

The invention concerns a mass flowmeter for measuring by means of the Coriolis principle both mass and density of a fluid flowing in pipes and establishing oscillations in these pipes, said mass flowmeter comprising an inlet and an outlet for the fluid, between which is arranged at least one measuring pipe, said measuring pipe being provided with sensors for the detection of movements in the measuring pipe in the form of fluid flow through the measuring pipe, said sensors consisting of at least one magnet fixed to the measuring pipe and at least one coil fixed to a coil supporting plate.

U.S. Pat. No. 5,349,872 describes a device of this kind. The magnets are arranged on a first measuring pipe and a second measuring pipe, and the coils are arranged on a frame for the mass flowmeter. Various ways of arranging the magnets and coils and various types of coils are described in the document. Measurements made with this device, which are described in the document, depend on the way the magnets are arranged on the measuring pipes and the type of coils used. Generally, the signal size will depend on the strength of the magnet and the size of the coil, so that a strong magnet will only demand a small coil and vice versa, to obtain a given signal size. The embodiments shown in the document are all realised with magnets fixed to the measuring pipes to reduce the mass of the measuring pipes and to facilitate the mounting of the cables leading to the coils. The mass of the magnets is normally smaller than the mass of the coils.

However, all the device embodiments shown in the document mentioned above imply one considerable disadvantage. The measurement accuracy depends among others on the linearity of the movement sensor described. The linearity again depends on the construction of the coil and the magnet. The coil in the embodiments shown are all made with one single winding. This implies that to get a linear signal, the magnet must be made so that it creates a homogenous field in the spot where the magnet influences the coil. This increases the complexity of the magnet, the weight increases, and the demands on positioning of magnet and coil are increasing. Further, the device can only make accurate measurements at a limited oscillation of the measuring pipes, as the linearity of the voltage induced in the coils only extends over a limited deflection of the measuring pipes.

SUMMARY OF THE INVENTION

The object of the invention is, therefore, to create a device, which does not bear this disadvantage, in that a given measurement accuracy is maintained even for large oscillations of the measuring pipes, in that the linearity of the voltage induced in the coils extends over a larger deflection of the measuring pipes, even with a simple magnet embodiment. This purpose should be reached without increasing the demands on mounting tolerances and thus the costs for mounting of this device compared with known devices.

This object is reached by a mass flowmeter, which is characterised in that at least one coil comprises a first winding and a second winding, and that the first winding is wound in one direction around a longitudinal axis, that the second winding is wound in a different, and opposite in relation to the first winding, direction around the longitudinal axis, that the first winding and the second winding are arranged axially in relation to each other along the longitudinal axis, and that the first winding is connected in series with the second winding.

A coil having these characteristics and used in a mass flowmeter implies that a given measurement accuracy of the mass flowmeter will be maintained even at large deflections of the measuring pipe, and at the same time the demand for mounting tolerances will be maintained and thus not increased.

A preferred embodiment of the mass flowmeter according to the invention is characterised in that the mass flowmeter comprises a first measuring pipe and a second measuring pipe, that at least a first and a second coil are fixed to the frame of the mass flowmeter, that at least a first magnet is fixed to the first measuring pipe and at least a second magnet is fixed to the second measuring pipe, that the first magnet on the first measuring pipe extends from the first measuring pipe outwards towards and inwards into the first coil on the frame and that the second magnet on the second measuring pipe extends from the second measuring pipe outwards towards and inwards into the second coil on the frame.

The invention is mainly meant for mass flowmeters with small dimensions on the measuring pipes, In which the mass of magnets and/or coils fixed to the measuring pipes is critical for the measuring accuracy of the mass flowmeter. The measuring pipe in the present invention has a cross-sectional area of less than 10 $mm^2$, preferably less than 3 $mm^2$. The device according to the invention with the stated magnet-coil construction can advantageously also be used as sensor pickup action between two pipes in larger mass flowmeters, as in the preferred embodiment the coil weighs 3.5 g with a magnet of 0.35 g, the major part of this weight originating from coil and coil body.

The preferred embodiment of the device according to the invention mentioned enables the highest degree of reduction of the mass and the highest degree of measuring accuracy of large deflections of the measuring pipes. Normally, the mass of the magnet is lower than the mass of the coil. Given that the coil is fixed to the frame of the mass flowmeter, the mass of the coil can be increased while the mass of the magnets can be decreased, without causing a deterioration of the measurement accuracy. At the same time the demand on mounting tolerances is decreased.

The positioning of the individual magnet in relation to the first winding and the second winding on the individual coil is important to obtain as high a degree of measurement accuracy as possible within as large deflections as possible of the measuring pipes.

In a preferred embodiment of magnet and coil the magnet is a bar magnet, and the coil is a ring coil. The ring coil is made by winding the first winding and the second winding around a coil body. The first winding and the second winding are displaced in relation to each other along a longitudinal axis of the ring coil. The magnet is placed between the first winding and the second winding with the polarity of the magnet directed along the longitudinal axis.

A displacement of the magnet along the longitudinal axis between the first winding and the second winding causes the induction of a voltage in both windings. As the first winding and the second winding have been wound in opposite directions around the longitudinal axis, the displacement of the magnet between the first winding and the second winding, and thus the induced voltage, have the same polarity.

BRIEF DESCRIPTION OF THE DRAWINGS

In the following the invention will be described on the basis of the enclosed drawings, showing:

FIG. 1 a schematic view, at right angles to the measuring pipes, of an embodiment of a mass flowmeter according to the invention FIG. 2 a schematic view, parallel to the measuring pipes, of the embodiment of a mass flowmeter according to the invention FIG. 3 a detailed sketch of measuring pipe, magnets and coils, shown in a preferred embodiment of the invention FIG. 4. a graphic view of an induced voltage in a coil as a function of a displacement of an armature FIG. 5 a graphic view of an induced voltage in both windings of a coil as a function of a displacement of an armature.

DESCRIPTION OF THE PREFERRED EMBODIMENTS

Figure 3:
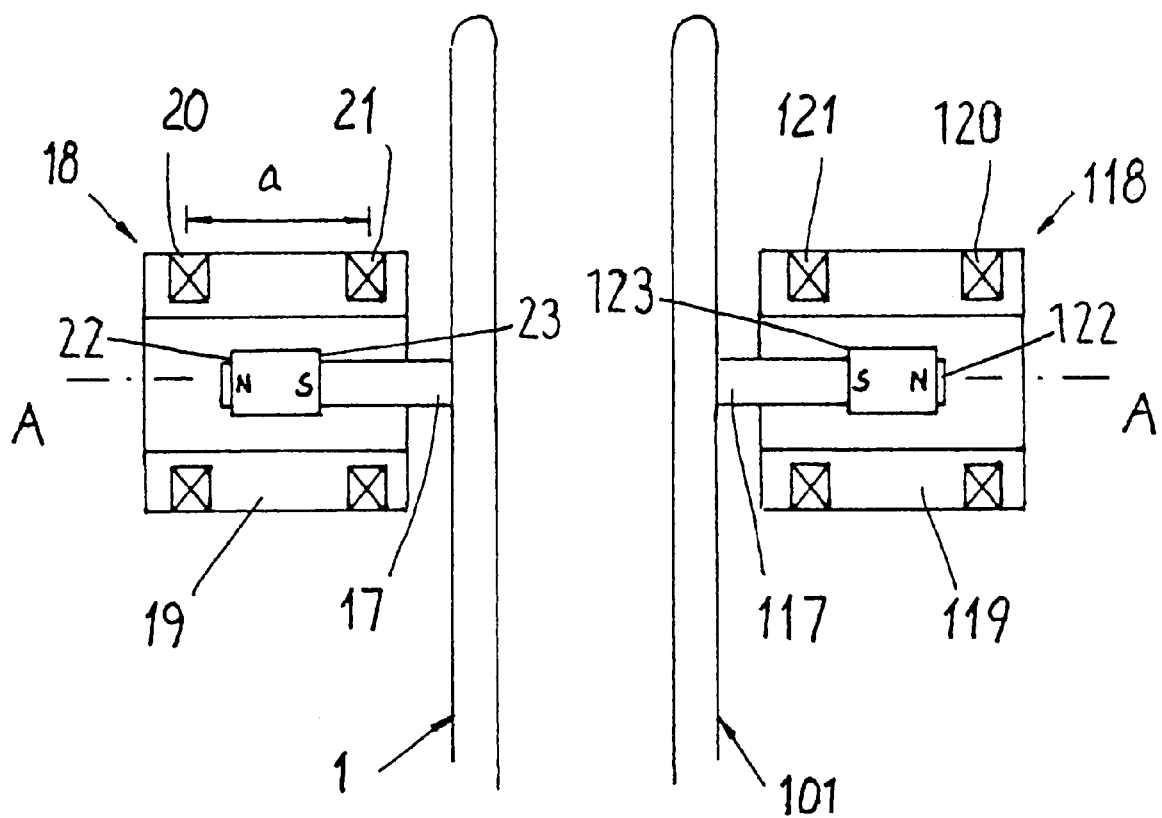

FIG. 1 shows a measuring pipe 1, extending between an inlet 2 and an outlet 3, and which is bent to a loop. An oscillation generator 4 is meant for making the measuring pipe 1 oscillate. A first oscillation detector 5 and a second oscillation detector 6 are meant for detecting oscillations of the measuring pipe 1. The oscillation detectors 5, 6 are placed at a distance before and a distance after the oscillation generator 4. The oscillation detectors 5, 6 comprise armatures in the shape of bar magnets, which are arranged displaceably in a ring coil (see FIGS. 2 and 3).

Oscillations of the measuring pipe 1 will cause the armatures to be displaced in relation to the coils, and a voltage will be induced in the coils. The induced voltage depends on the oscillations of the measuring pipe and is converted to a measurement value. The oscillations of measuring pipe 1, and in particular a phase difference between individual oscillations of two measuring pipes, give a very high accuracy when fixing the mass of a fluid flowing through the pipes. This applies for measurements made on the basis of the Coriolis principle, as well as for measurements in which surges in the pipe walls of measuring pipe 1 play a role, and measurements using other methods, which depend on the oscillations of the measuring pipe.

The measurement values are treated in an electrical circuit 7, using the influence from the oscillation generator 4 and the measurement values for the oscillations detected by the oscillation detectors 5, 6 for fixing the mass of the fluid flowing through measuring pipe 1.

Together with the oscillation generator 4 and the oscillation detectors 5, 6 the measuring pipe is arranged in a housing 8 with an inside 9, which is evacuated, and has an underpressure compared with the atmosphere. The pressure on the inside 9 is essentially lower than 0.1 bar. The measuring pipe 1 has a very small inner cross-sectional area of less than 10 mm$^2$, preferably less than 3 mm$^2$. The combination of an underpressure on the inside 9 of the housing 8 and the very small inner cross-sectional area of measuring pipe 1 implies that measurements of even very small masses of fluid flowing through the measuring pipe 1 can be effected with a high accuracy.

The measuring pipe 1 runs through a bottom 10 in the housing 8 at the fixing spots 11, 12. The fixing spots 11, 12 have been chosen so that nodal centres of oscillation of the measuring pipe 1 are found in the fixing spots 11, 12. Thus, oscillation energy is not transferred to the housing 8 via the fixing spots 11, 12. A plug connection 13 is arranged in a wall of the housing 8. As shown, the electrical circuit 7 is connected with the oscillation detector 6, but also with the oscillation generator 4 and the oscillation detector 5, which is not shown, however.

FIG. 2 shows that in the housing 8 another measuring pipe 101 is arranged, which has the same design as measuring pipe 1. The measuring pipes 1, 101 are connected with each other via a connection plate 14. The oscillation generators 4, 104 are electromotors with induction coils 15, 115 which are supplied with AC-current, and armatures 16, 116 in the form of magnets. The AC-current in the induction coils 15, 115 has a frequency corresponding to the working frequency of the measuring pipes 1, 101. The armatures 16, 116, which are fixed to the measuring pipes 1, 101, transfer the oscillation movement to the measuring pipes.

Besides, other oscillation detectors 105, (not illustrated, but identical to the detector 5) 106 are provided, which have the same design as the oscillation detectors 5, 6. The armatures 17, 117, which are arranged on the measuring pipes 1, 101, influence the coils 18, 118 so that a voltage corresponding to the transferred oscillation frequency is induced. The second measuring pipe 101 is passed in the same direction as the measuring pipe 1 by a fluid to be measured, but oscillations are generated in the reverse phase of measuring pipe 1. This leads to better measurement results, as this eliminates a possible unbalance.

The housing 8 is made of steel or another metal. The plug connection 13, which is fixed to the housing 8, can have different designs, e.g. it can be made like the electrical entry on hermetically enclosed small refrigeration machines.

FIG. 3 is a detailed sketch of the oscillation detectors 5, 105, alternatively 6, 106 for a mass flowmeter according to the invention. The oscillation detectors comprise the armature 17, 117 and the coil 18, 118. In the embodiment shown, the coil 18, 118 is a ring coil with a coil body 19, 119, and the armature 17, 117 is a bar magnet.

The coil 18, 118 is provided with a first winding 20, 120 and a second winding 21, 121. The first winding 20, 120 and the second winding 21, 121 are arranged at a distance a from one another along a longitudinal axis A. The first winding 20, 120 is wound around the longitudinal axis A in a first direction of rotation. The second wind 21, 121 is also wound around the longitudinal axis, but, compared with the first winding 20, 120, in the opposite direction of rotation.

The armature 17, 117 is fixed on the measuring pipe 1 and extends outwards and inwards in the coil 18, 118. The armature 17, 117 is arranged between the first winding 20, 120 and the second winding 21, 121 with the polarity of the armature 17, 117 directed along the longitudinal axis A. A north pole 22, 122 is directed towards the first winding 20, 120 and a south pole 23, 123 is directed towards the second winding 21, 121. As mentioned, induction of voltages in the coil 18, 118 takes place in that the armature 17, 117 is displaced along the longitudinal axis A, when the measuring pipe 1 starts oscillating and a fluid flows through the measuring pipe 1.

Figure 4:
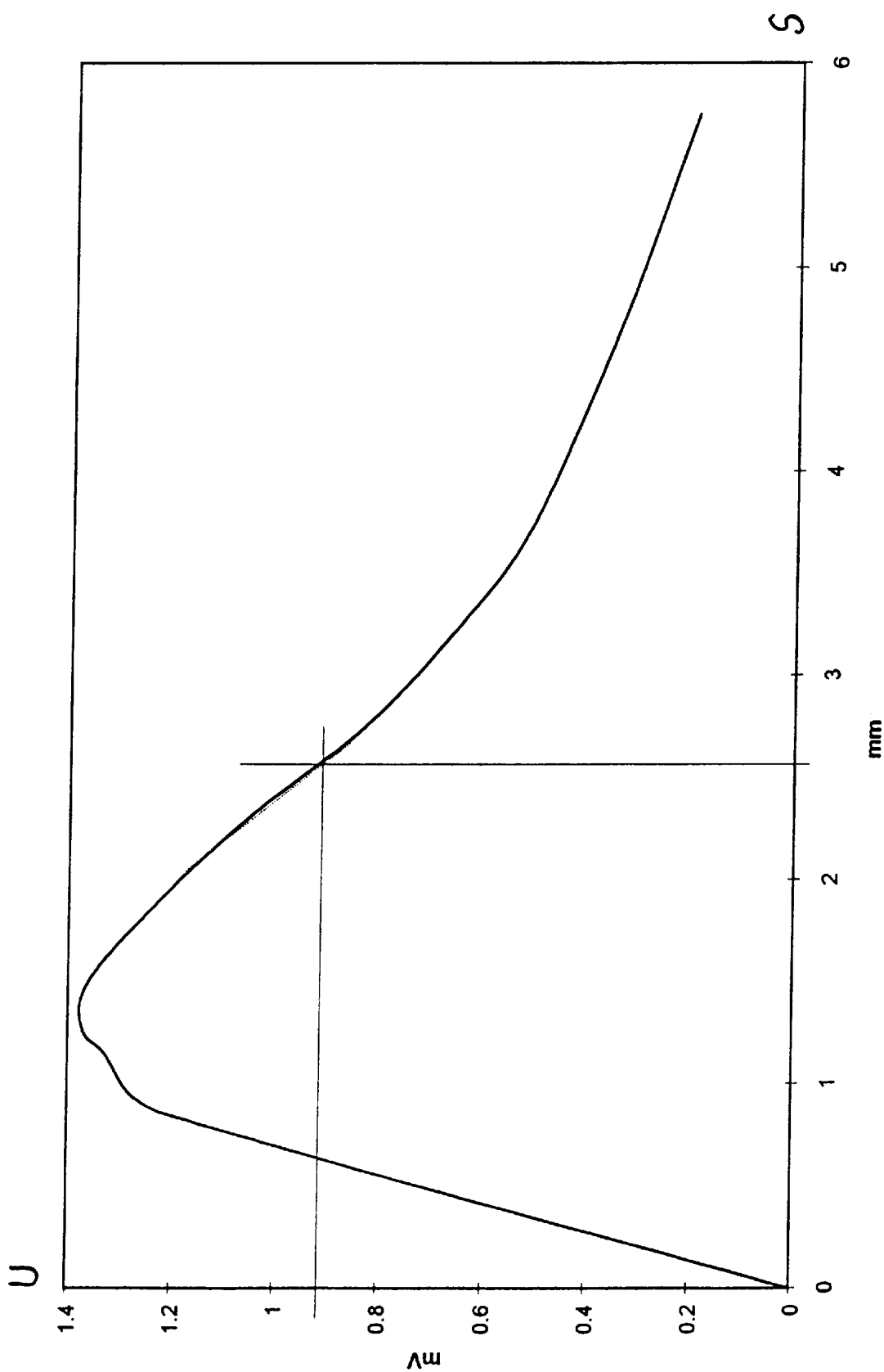

FIG. 4 is a graphical illustration of a induced voltage U as a function of a displacement S of the armature in a single winding of the coil 18, 118. The graph illustrates the voltage U, which is induced in one winding, either the first winding 20, 120 or the second winding 21, 121, by displacement of the armature 17, 117 in the coil 18, 118 along the longitudinal axis A. It appears from the graph that the induced voltage U increases linearly by a displacement of the armature from 0 mm to about 1 mm. In a position of the armature 17, 117 corresponding to a displacement of about 1.5 mm, the graph of the induced voltage U has a peak. After the peak the graph of the induced voltage U decreases evenly at a further displacement of the armature 17, 117 along the longitudinal axis A. In a position of the armature corresponding to a displacement of about 2.5 mm, the graph of the induced voltage U has a deflection tangent. The accuracy of measurements of the induced voltage is highest in positions around this deflection tangent. An introductory positioning of the armature 17, 117 in the coil 18, 118, when the armature 17, 117 is not influenced by oscillations from the oscillation generator 4 or from fluid flowing through the measuring pipes, should therefore be made in accordance with a displacement of about 2.5 mm. Displacements taking place on oscillations of the measuring pipe 1 will cause that the armature will be displaced along the longitudinal axis around the position 2.5 mm.

The graph of the induced voltage U has multi-order links, also in the position around 2.5 mm. To maintain a given measuring accuracy, it is necessary that the measurements are made as close to the deflection tangent as possible, to get the largest possible reduction of the influence from multi-order links. By using coils 18, 118 with a first winding 20, 120 and a second winding 21, 121, wound in opposite directions around the longitudinal axis A, it can be reached that the influence from multi-order links is reduced considerably. This causes a considerable increase in the measuring accuracy, especially in the position around the deflection tangent.

Figure 5:
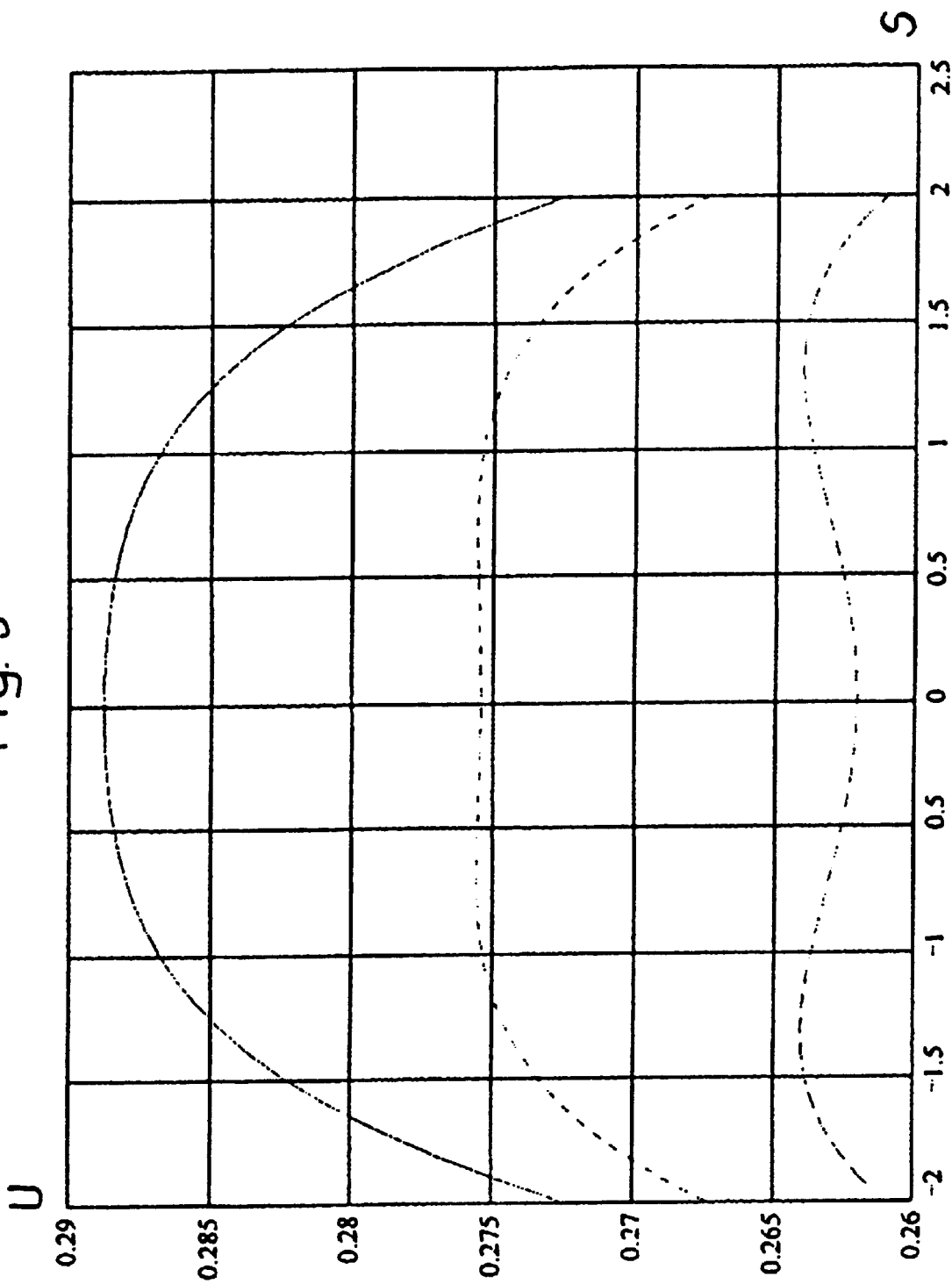

FIG. 5 is a graphical illustration of an induced voltage U as a function of a displacement S of the armature in both windings of the coil 18, 118. The graph illustrates the voltage U induced in the coil as a whole by a displacement of the armature 17, 117 in the coil 18, 118 along the longitudinal axis A. The graph illustrates the voltage U induced in a first coil at a distance a between the windings of 4.8 mm, in a second coil at a distance a between the windings of 5.0 mm, and in a third coil at a distance a between the windings of 5.2 mm.

It appears from the graph that the graph of the induced voltage U in the first coil increases evenly at a displacement of the armature from −2 mm to 0 mm, which means from a position at a left winding to a position in the middle of the coil. In a position of the armature 17, 117 corresponding to a displacement of 0 mm, meaning the middle of the coil, the graph of the induced voltage U has a peak. After the peak the graph of the induced voltage U decreases evenly at a further displacement of the armature 17, 117 along the longitudinal axis A from 0 mm to +2 mm, meaning from the middle of the coil to a position at a right winding.

The graph of the induced voltage U in the second coil increases evenly at a displacement of the armature from −2 mm to about −0.8 mm, i.e. from a position at a left winding to a position between the left winding and the middle of the coil. In a position of the armature 17, 117 corresponding to a displacement from −0.8 mm to +0.8 mm, i.e. from a position between the left winding and the middle of the coil to a position between the middle of the coil and the right winding, the graph of the induced voltage U has an approximately constant value of about 0.275 V. After the course with the constant value, the graph of the induced voltage U decreases evenly at a further displacement of the armature 17, 117 along the longitudinal axis A from +0.8 mm to +2 mm, i.e. from a position between the middle of the coil and the right winding to a position at the right winding.

The graph of the induced voltage in the third coil increases evenly at a displacement of the armature from −2 mm to about −1.4 mm, i.e. from a position at a left winding to a position between the left winding and the middle of the coil. In a position of the armature 17, 117 corresponding to a further displacement from −1.4 mm to 0 mm, i.e. from a position between the left winding and the middle of the coil to a position in the middle of the coil, the graph of the induced voltage U decreases. In a position of the armature 17, 117 corresponding to a displacement from 0 mm to +1.4 mm, i.e. from the middle of the coil to a position between the middle of the coil and the right winding, the graph of the induced voltage U increases. In a position of the armature 17, 117 corresponding to a further displacement from +1.4 mm to +2 mm, i.e. from a position between the middle of the coil and the right winding to a position at the right winding, the graph of the induced voltage U decreases.

The accuracy of measurements of the induced voltage is highest in positions around the middle of the coil. An initial positioning of the armature 17, 117 in the coil 18, 118, when the armature 17, 117 is not influenced by oscillations from the oscillation generator 4 or from fluid flowing in the measuring pipes, should therefore take place at a displacement corresponding to about 0 mm. Displacements made with oscillating measuring pipe 1 will imply that the armature 17, 117 will be displaced along the longitudinal axis around the position 2.5 mm. An optimum distance a between the windings is established through tests.

Figure 6:
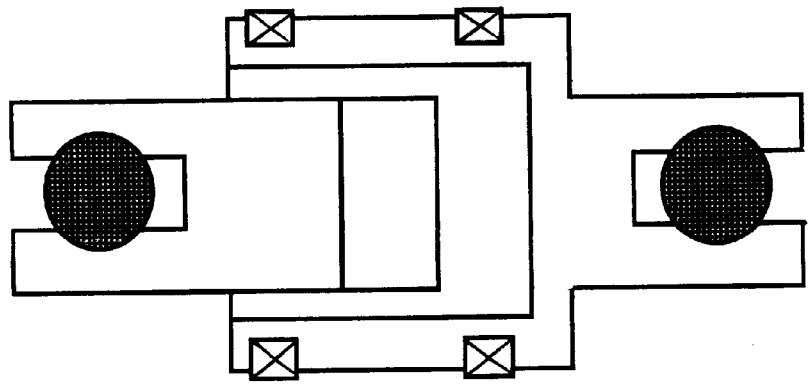
FIG. 6 A schematic view of an alternative embodiment of the invention having one coil secured to one measuring pipe and one magnet secured to the other measuring pipe.
Figure 7:
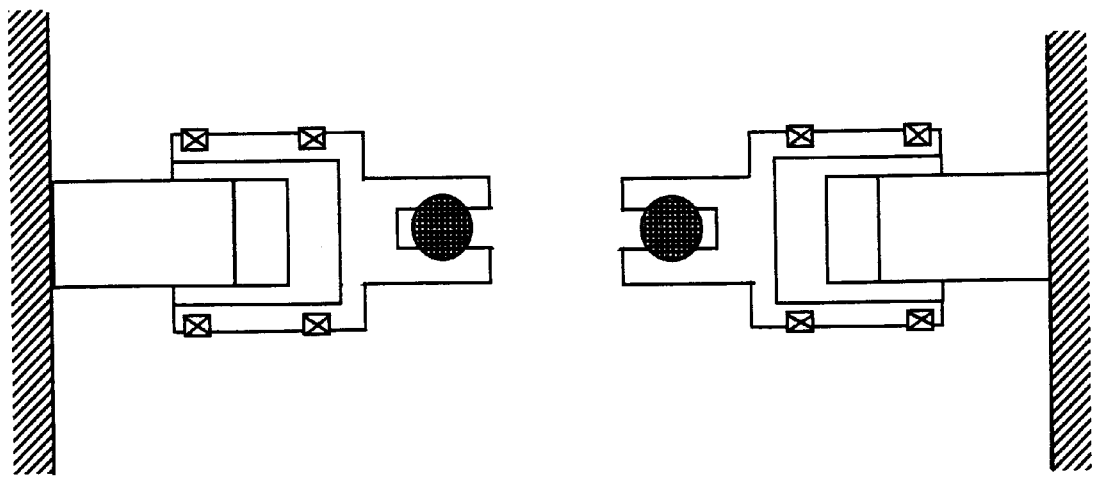
FIG. 7 A schematic view of a further embodiment of the invention in which the magnets are secured to the frame and the coils are secured to the measuring pipes.

In the above, the invention is described with reference to a specific embodiment of a mass flowmeter according to the invention. Other embodiments can be produced. The armatures 17, 117 can be fixed on the housing and the coils on the measuring pipes as shown in FIG. 6. The armatures 17, 117 can also be fixed on the first measuring pipe 1, and the coils 18, 118 can be fixed on the second measuring pipe 101 as shown in FIG. 7. One measuring pipe, e.g. the first measuring pipe 1, can be fixed to the housing 8, and the second measuring pipe 101 can be fixed at the fixing spots 11, 12. The measuring pipes 1, 101 can be bent into a loop with a different shape than the one in the shown embodiment.

What is claimed is:

1. Mass flowmeter for measuring by means of the Coriolis principle both mass and density of a fluid flowing in pipes and establishing oscillations in the pipes, said mass flowmeter comprising an inlet and an outlet for the fluid, at least one measuring pipe being located between the inlet and the outlet, said measuring pipe having sensors for the detection of movements in the measuring pipe in the form of fluid flow through the measuring pipe, said sensors comprising at least one magnet fixed to the measuring pipe and at least one coil fixed to a coil supporting plate, at least one of the coils comprising at least one first winding and one second winding, the first winding being wound in one direction around a longitudinal axis, the second winding being wound in another, and in relation to the first winding, opposite direction around the longitudinal axis, the first winding and the second winding being located axially in relation to each other along the longitudinal axis, and the first winding being connected in series with the second winding.

2. Mass flowmeter according to claim 1, in which the flowmeter comprises two measuring pipes, the measuring pipes having a circular inner cross-section, and the cross-sectional area of the measuring pipes being smaller than 10 mm$^2$.

3. Mass flowmeter according to claim 2, in which the cross-sectional area of the measuring pipes is smaller than 3 mm$^2$.

4. Mass flowmeter according to claim 1, in which the measuring pipe extends in a loop with a mainly triangular shape, with a first side extending from a first corner at the inlet diagonally upwards to a second corner, a second side extending from the second corner mainly horizontally to a third corner, and a third side extending diagonally downwards from the third corner to the first corner.

5. Mass flowmeter according to claim 4, in which the measuring pipe includes a first magnet, which is fixed to the first side, a second magnet, which is fixed to the second side, and a third magnet, which is fixed to the third side.

6. Mass flowmeter according to claim 1, comprising a first measuring pipe and a second measuring pipe, at least one coil secured to the first measuring pipe, at least one magnet secured to the second measuring pipe, and the magnet on the second measuring pipe extending outwardly from the second measuring pipe and into the coil on the first measuring pipe.

7. Mass flowmeter according to claim 1, in which at least one coil is fixed to a frame of the mass flowmeter, at least one magnet is fixed to a measuring pipe, and the magnet on the measuring pipe extends outwardly from the measuring pipe and into the coil on the frame.

8. Mass flowmeter according to claim 1, comprising a first measuring pipe and a second measuring pipe, at least one first coil and one second coil being secured to a frame of the mass flowmeter, at least one first magnet being secured to the first measuring pipe, at least one second magnet being secured to the second measuring pipe, the first magnet on the first measuring pipe extending outwardly from the first measuring pipe and into the first coil on the frame, and the second magnet on the second measuring pipe extending outwardly from the second measuring pipe and into the second coil on the frame.

9. Mass flowmeter according to claim 1, in which at least one coil is a ring coil wound on a coil body, at least one magnet has a circular cylindrical shape and the magnet extends into the coil such that the magnet is located between a first winding and a second winding of the ring coil.

10. Mass flowmeter according to claim 9, in which the coil body comprises a cylinder with a first end face and a second end face, at least a first track and a second track extend along a surface of the cylinder around a longitudinal axis, and the first track is displaced in relation to the second track along the longitudinal axis.

11. Mass flowmeter for measuring by means of the Coriolis principle both mass and density of a fluid flowing in pipes and establishing oscillations in the pipes, said mass flowmeter comprising an inlet and an outlet for the fluid, at least one measuring pipe being located between the inlet and the outlet, said measuring pipe having sensors for the detection of movements in the measuring pipe in the form of fluid flow through the measuring pipe, said sensors comprising at least one magnet and at least one coil fixed to a coil supporting plate, at least one of the coils comprising at least one first winding and one second winding, the first winding being wound in one direction around a longitudinal axis, the second winding being wound in another, and in relation to the first winding, opposite direction around the longitudinal axis, the first winding and the second winding being located axially in relation to each other along the longitudinal axis, and the first winding being connected in series with the second winding, and in which at least a first magnet and a second magnet are secured to a frame of the mass flowmeter, at least a first coil is secured to the first measuring pipe, at least a second coil is fixed to the second measuring pipe, the first magnet on the frame extending outwards from the frame and into the first coil on the first measuring pipe, and the second magnet on the frame extending outwardly from the frame and into the second coil on the second measuring pipe.

* * * * *